United States Patent
Gjerde et al.

(10) Patent No.: US 9,891,148 B2
(45) Date of Patent: *Feb. 13, 2018

(54) METHOD AND APPARATUS FOR PIPETTE TIP COLUMNS

(71) Applicants: Douglas T. Gjerde, Saratoga, CA (US); Lee Hoang, Santa Clara, CA (US); Chris Suh, San Jose, CA (US); Mark Abel, San Jose, CA (US)

(72) Inventors: Douglas T. Gjerde, Saratoga, CA (US); Lee Hoang, Santa Clara, CA (US); Chris Suh, San Jose, CA (US); Mark Abel, San Jose, CA (US)

(73) Assignee: Douglas T. Gjerde, Saratoga, CA (US)

( * ) Notice: Subject to any disclaimer, the term of this patent is extended or adjusted under 35 U.S.C. 154(b) by 123 days.

This patent is subject to a terminal disclaimer.

(21) Appl. No.: 14/846,825

(22) Filed: Sep. 7, 2015

(65) Prior Publication Data

US 2016/0061697 A1  Mar. 3, 2016

Related U.S. Application Data

(63) Continuation of application No. 13/023,519, filed on Feb. 8, 2011, now Pat. No. 9,242,244, which is a
(Continued)

(51) Int. Cl.
*G01N 1/34* (2006.01)
*B01L 3/00* (2006.01)
(Continued)

(52) U.S. Cl.
CPC ............... *G01N 1/34* (2013.01); *B01L 3/021* (2013.01); *B01L 3/5085* (2013.01); *G01N 1/40* (2013.01);
(Continued)

(58) Field of Classification Search
CPC ........ B01L 3/02; B01L 3/5085; B01L 3/0275; B01L 2400/0487; B01L 2300/0681;
(Continued)

(56) References Cited

U.S. PATENT DOCUMENTS

| 9,242,244 B2 * | 1/2016 | Gjerde | ...................... B01L 3/02 |
| 9,370,732 B2 * | 6/2016 | Gjerde | ................... G01N 1/405 |
| 9,637,719 B2 * | 5/2017 | Gjerde | ..................... C12N 1/02 |

* cited by examiner

Primary Examiner — Christopher Adam Hixson
(74) Attorney, Agent, or Firm — Sue S. Kalman

(57) ABSTRACT

An apparatus and method of using a pipette with pipette tip columns were developed in which a pipette is operated with the pipette tip columns inserted into the wells of a microplate. In this configuration the pipette is free standing and is essentially perpendicular to the microplate. The pipette is hand-held when transferring between positions, e.g., between operation steps that take place in different rows of wells. The open lower ends of the pipette tip column are approximately centered within the plate well. The columns and plate are designed in such a way that the open lower ends of the pipette tip columns are in contact with liquid in the plate well however, the columns do not seal on the well bottom, preventing flow in and out of the column. The pipette contains the appropriate firmware and software to control flow for all steps of pipette tip column operation. In some embodiments, cells are purified from biological samples.

22 Claims, 4 Drawing Sheets

Related U.S. Application Data continuation-in-part of application No. 14/181,656, filed on Feb. 15, 2014, now Pat. No. 9,370,732, application No. 14/846,825, filed on Sep. 7, 2015, which is a continuation-in-part of application No. PCT/US2014/016637, filed on Feb. 15, 2014, application No. 14/846,825, filed on Sep. 7, 2015, which is a continuation-in-part of application No. 14/563,994, filed on Dec. 8, 2014, now Pat. No. 9,637,719, application No. 14/846,825, filed on Sep. 7, 2015, which is a continuation-in-part of application No. PCT/US2015/024374, filed on Apr. 3, 2015.

(60) Provisional application No. 61/302,851, filed on Feb. 9, 2010, provisional application No. 61/765,541, filed on Feb. 15, 2013, provisional application No. 61/832,501, filed on Jun. 7, 2013, provisional application No. 61/858,054, filed on Jul. 24, 2013, provisional application No. 61/873,828, filed on Sep. 4, 2013, provisional application No. 61/913,154, filed on Dec. 6, 2013, provisional application No. 61/913,190, filed on Dec. 6, 2013, provisional application No. 62/061,636, filed on Oct. 8, 2014, provisional application No. 61/974,950, filed on Apr. 3, 2014.

(51) Int. Cl.
*B01L 3/02* (2006.01)
*G01N 1/40* (2006.01)

(52) U.S. Cl.
CPC ........... *B01L 3/0237* (2013.01); *B01L 3/0275* (2013.01); *B01L 2200/025* (2013.01); *B01L 2200/0631* (2013.01); *B01L 2300/0681* (2013.01); *B01L 2300/0829* (2013.01); *B01L 2400/0487* (2013.01); *Y10T 436/255* (2015.01)

(58) Field of Classification Search
CPC ..... B01L 2300/0829; B01L 2200/0631; G01N 1/34; C12N 15/1003
See application file for complete search history.

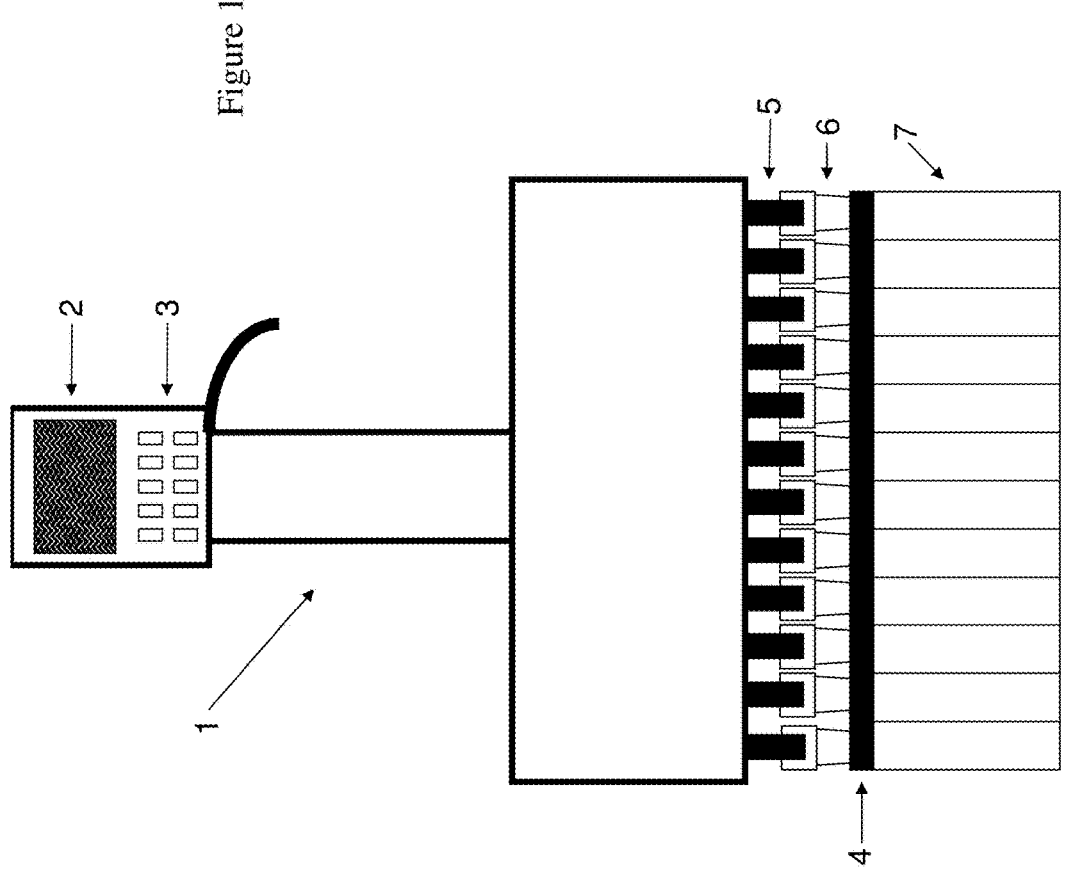

Figures 2A-2B
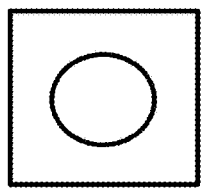
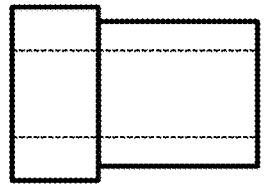
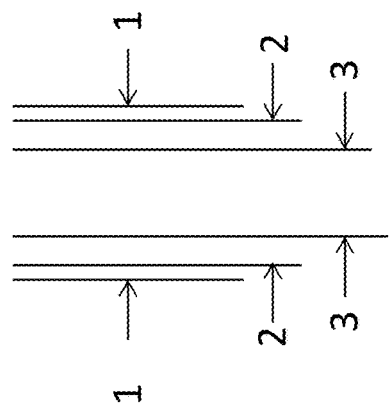
2A 2B

METHOD AND APPARATUS FOR PIPETTE TIP COLUMNS

CROSS REFERENCE TO RELATED APPLICATIONS

This application claims priority to and benefit of U.S. Provisional Patent Application No. 61/302,851 filed Feb. 9, 2010, the disclosure of which is incorporated herein by reference in their entirety for all purposes.

BACKGROUND OF THE INVENTION

Pipette tip columns contain functionalized solid material in a column formed at the end or lower part of the tips. The columns are used to separate and purify sample materials from a variety of sources including biological samples and environmental samples. Pipette tip columns are often used with robotic liquid handlers. However, robotic liquid handlers can cost up to several hundred thousand dollars which is a very large of investment for many users. Therefore, there is a need for a simplified, lower cost, lower throughput means for reliable operation of pipette tip columns.

SUMMARY OF THE INVENTION

An apparatus and method of using a freestanding pipette with pipette tip columns were developed. The pipette tip columns are used for performing separations such as solid phase extraction. The pipette is operated with the pipette tip columns inserted into the wells of a multiwell microplate. In this configuration the pipette is freestanding and will not tip over. The open lower ends of the pipette tip columns are approximately centered within the plate well. The columns and plate are designed in such a way that the open lower ends of the pipette tip columns are in contact with liquid in the plate well, however, the columns do not seal on the well bottom, which would prevent flow in and out of the column. The pipette contains the appropriate firmware and software to control flow for all steps of pipette tip column operation.

BRIEF DESCRIPTION OF THE FIGURES

FIG. 1 depicts a standless, freestanding hand-held multi-channel pipette and deep-well plate embodiment of the invention.

FIG. 2A is a depiction of the top view of a single well plate modifier, and FIG. 2B depicts a side view thereof.

DETAILED DESCRIPTION OF THE INVENTION

Figure 3A:
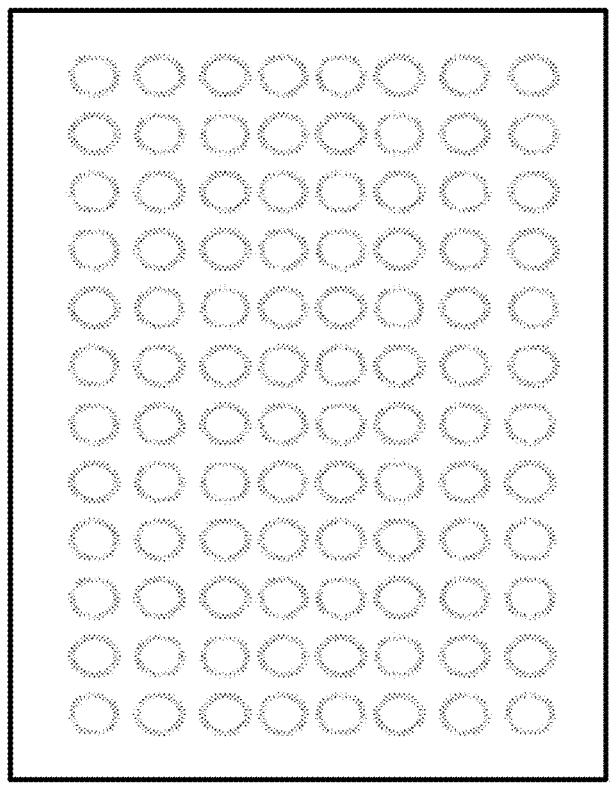
FIG. 3A is a top-down view and FIG. 3B is a side view of an embodiment of a multi-well plate modifier which may be used with the embodiment of FIG. 1.

The present invention provides a device and method for performing separations with a pipette tip column. The device is a hand-held freestanding pipette that can operate a plurality of columns simultaneously in combination with pipette tip columns and a microplate. For the purposes of this disclosure, a "hand-held freestanding pipette" is defined as follows: the pipette can be freestanding when it is placed in position, e.g., in a deepwell plate, and does not require being supported by a stand or a hand in order to function properly. The pipette is hand-held when transferring between positions, e.g., between operational steps that take place in different rows of wells.

In the methods of the invention, a material or analyte (or analytes) can be purified from a sample. Typically, the methods involve the steps of capture, wash (to remove contaminants) and elution to obtain the purified material, however, there are some methods in which the wash step can be omitted. In certain embodiments, an electronic pipette of the invention contains software and firmware that enables the steps of capture, wash and elution/recovery in one operational method or program without a physical connection to a computer.

An advantage of the pipette of the invention is that it can perform parallel operation of multiple pipette tip columns yet it is significantly less expensive than a robotic liquid handling system. Another benefit of the device is that it is similar in size to a multichannel pipette and therefore does not occupy much laboratory bench space. An additional advantage of the pipette of the invention is that it is freestanding. That is, a stand is not required for its operation.

Although it is desirable to operate pipette tip columns with a handheld electronic pipette, commercially-available existing electronic pipettes have limited keyboards and displays and limited software, firmware, memory and microprocessing capabilities. PhyNexus, Inc. (San Jose, Calif.) sells the ME200 and ME1000 Purification Systems for semi-automated processing of 1-12 samples at a time. These systems are comprised of a pipette held in place on a stand and controlled via Windows-based software. The ME system allows automated programming of an 8 or 12 channel pipette with complete purification of up to 12 samples in as little as 15 minutes.

The ME Purification System is quite useful, however, the instant invention offers some improvements. Although the ME pipette stand system is much lower cost than robotic liquid handlers, the investment is still several thousand dollars. It can be difficult to adjust the ME and it can be complicated to use. The ME pipette technology is based on a computer controlled pipette that is placed in a stand and connected to the computer through a cable. The computer was needed because the software was too complex and lengthy for loading onto an electronic pipette. However, the presence of the cables can be cumbersome, and a self-contained device is preferable. Furthermore, the ME requires manual adjustment of the z-position which can be time-consuming and runs the risk of being inaccurate.

Therefore, there exists a need for a device (and accompanying method) in which the lower end of the pipette tip column(s) is centered in a microplate well or tube at the proper height for pipetting small volumes of liquid. This device should hold the pipette tip column at the appropriate height to prevent sealing the lower end of the column against the well bottom. Additionally, the device should not require manual adjustment.

To overcome the drawbacks of existing systems, an apparatus and method of using a pipette with pipette tip columns were developed. The apparatus is a free-standing or standless pipette with pipette tip column(s) containing firmware, software and firmware control capable of going through all the steps of purification with pipette tip columns and a deep-well plate. The columns and plate are designed to match so that the pipette with pipette tip columns attached stands vertically when placed in the plate and does not tip over. The columns and plate are designed so that the ends of the pipette tip columns are substantially self centering but do not seal on the plate bottom.

Several factors had to be developed, solved, tested, and verified in order to be able to use the standless electronic pipette, pipette tip column and microplate of the invention. It is counterintuitive to operate a pipette without holding it. In fact, electronic pipettes are also called handheld pipettes; their name describes what they are, how they are designed and how they are used. Obviously, if a pipette holding pipette tip columns is not supported, the pipette and columns will fall over. In addition, pipette tip columns usually require several steps of operation with different solutions which requires moving the pipette to a series of vials or wells. These steps are traditionally done with the firm support of a hand.

A series of experiments was performed in an attempt to balance the pipette and pipette tip columns with minimum support. It was found that the most favorable balancing of the pipette could be achieved by keeping the pipette as close to vertical as possible. If the pipette was positioned at an angle, then the off-center weight of the pipette would simply pull the whole apparatus over.

The second problem was maintaining the pipette with pipette tip columns in a (more or less) vertical position without a stand or support. The initial solution to this problem was the use of deep-well plates designed to fit the size of the columns. However, pipetting operations are not usually performed by simply placing a pipette into a deep-well plate. The bottom of the pipette tip could seal and prevent flow. Coating the outside of the wall of the pipette tip with liquid could increase the volume of solution aspirated or could contaminate the solution. The same problem could be expected when pipette tip columns were substituted for pipette tips.

A third potential problem was the weight of the pipette pushing the lower end of the pipette tip columns too far down into the well, sealing the end of the columns and preventing flow in and out of the column. In hand-held pipetting operations, the pipette tip can be held at an angle to prevent sealing of the bottom of the tip. In a robotic system, the tips come straight down but the depth or z-axis position is controlled by computer so that the ends of the tips do not come down too far, sealing the ends of the columns.

The size of the plate, the diameter of the wells, shape of the wells relative to the diameter of the pipette columns were chosen to keep the pipette and pipette tip columns more or less vertical and stable from falling when placed into the deep-well plate. It was found that increasing the depth of the wells in 96-well deep-well plates could keep the columns more or less vertical. In certain embodiments, the deep well plates are in the range of 20 mm to 45 mm. In some embodiments the height of the plate is at least 22 mm, at least 27 mm, at least 31 mm, at least 41 mm, at least 42 mm, at least 43 mm or at least 44 mm.

The diameter of the column relative to the opening also had to be considered although as the depth of the well was increased the diameter of the well relative to the column became less important. The diameter of the columns could not be too small relative to the diameter of the wells in the plate. Inserting the pipette with column or columns into the deep-well plate kept the pipette from tipping by keeping it standing more or less vertical. If the pipette is at an angle more than 25-45 degrees from vertical, it would likely not be stable. In preferred embodiments, the angle of the pipette is 35 degrees or less from vertical (perpendicular to the plate). For example, the angle of the pipette can be less than 35 degrees, less than 30 degrees, less than 25 degrees, less than 20 degrees, less than 15 degrees, less than 10 degrees, less than 5 degrees, less than 4 degrees, less than 3 degrees, less than 2 degrees or less than 1 degree from vertical.

In preferred embodiments, the plate is a 96-well deep-well microplate in ANSI or SBS format. In other embodiments, a non-standard plate format or even a custom plate could be used. In certain embodiments, the plate could have fewer or more than 96 wells. In those embodiments, the plate could be comprised of 6, 12, 24, 48, 192 or 1536 wells.

In certain embodiments, the microplates used have quite shallow wells and are not considered deep-well plates. In these embodiments, the plate height can be less than 22 mm, less than 20 mm, less than 10 mm or even less than 5 mm. In still another embodiment, tubes or vials can be substituted for a microplate.

A fourth problem to be solved was programming the pipette specifically for operation of pipette tip columns. Pumping solutions through pipette tip columns is quite different from simply aspirating and expelling liquids. The presence of the solid phase in the tip can give the column back pressure. In preferred firmware and software embodiments, time pauses are programmed at the end of some aspiration and expel pumping strokes. This is preferred if there is appreciable column backpressure and the flow through the column is slowed or delayed from the pumping stroke.

Sometimes, engagement of the pipette tip column with the pipette can create a positive pressure. This is particularly true when the column has high backpressure, for example, if the solid phase is wet such as is the case when using a hydrated gel resin and air cannot pass through the bed. If a positive pressure is present, programming may be used to compensate for this initial buildup of pressure. Pressure buildup on insertion of the column onto the pipette and column backpressure can increase as the column diameter decreases.

Expulsion of extra volumes at the end of each capture cycle and each wash cycle may be useful to ensure all of the liquid on top of the column bed is expelled before the column is moved to the next solution. But care must be taken as it is preferred that no air enter the bed of the pipette column even if extra pump volumes are used. Often, slower flow rates are used when pumping solutions through pipette tip columns than when simply aspirating and expelling liquids in an empty pipette tip.

Electronic pipettes often include a blow out at the end of the expulsion stroke to ensure that the liquid inside the tip is expelled. This operation is often included in the firmware and software and cannot be modified by the user. But the blow out may not be compatible with pipette tip column operation. The intake of liquid in the next stroke may be hindered by the introduction of air into the column bed by the blow out. The blow out may prevent or partially disrupt the aspiration of the liquid into the pipette tip column.

Most often, pipette tip columns are operated with back and forth flow. That is, liquids are aspirated and expelled only through the open lower end of the column. However, in certain embodiments of the present invention, liquids can enter the column at the upper end and exit through the lower end, flowing in a single direction. In these embodiments, liquid may be added to the top of the pipette tip column and the pipette may be engaged to push liquid through the column. The pipette tip columns may be used for extraction and chromatography and may employ a number of different column chemistries.

In certain embodiments, the pipette tip columns may be used in a several step process. After an optional conditioning of the column, the column may be placed into a sample. One or more analytes from the sample can be captured by the solid phase within column with back and forth flow. Several capture buffer solution conditions and/or several column types may be surveyed by operating the columns in parallel.

After capture and expulsion of the sample liquid, the column can be placed into a wash solution to remove impurities. In some embodiments several different washes may be used to remove different types of bound or entrained impurities. Again, the effectiveness of different wash buffers may be surveyed by operating the pipette tip columns in parallel. In certain embodiments, the wash solution may be removed from the column with a water or saline solution to facilitate introduction of an acid elution solution.

The final step of extraction is elution of the purified analyte. The elution may be performed with serial increases with elution solvent strength to determine the optimum eluting solvent. In this embodiment, conditions may be identified that elute the compound of interest while retaining impurities. Several elutions can be performed to ensure the complete removal of the purified analyte.

All of these operations result in requirements of an electronic pipette that are quite different from simply aspirating and expelling liquids.

FIG. 1 depicts a 12-channel pipette of the invention (reference no. 1). The top of the pipette has display 2 and buttons for programming 3. The pipette barrels 5 are engaged with pipette tip columns 6 which are submerged in deep well plate 7. An optional attachment 4 to the plate or columns keeps the columns centered within each well. Although the pipette depicted in FIG. 1 is a 12-channel electronic pipette, this is not required. Although it is not preferred, the standless pipette could also be a manual pipette. Likewise, the standless pipette of the invention could also be a single-channel electronic pipette.

Furthermore, the standless pipette need not be limited to having the dimensions of those that are commercially available. The geometry of the standless pipette can be changed to suit the invention.

In some cases, the diameter of the pipette tip column is considerably smaller than an unmodified plate. In some cases, this will cause the pipette tip column and pipette to tilt from vertical causing the combination of pipette, pipette tip column and plate to tip. FIG. 2A shows the top view and FIG. 2B shows the side view of a plate modifier or adapter which can prevent the pipette tip column and pipette from tilting and tipping. A single plate adapter can be used with a single pipette tip column inserted into a deep well plate, such as a 96-well microplate. The lower end of the plate adapter has width 2 which fits into the well while the upper part of the adapter having width 1 sits above the well. If the well is in a standard 96-well plate, width 2 can be, for example, 8 mm while width 1 can be, for example, 9 mm. The hole in the center of the adapter has width 3 which allows insertion of the pipette tip column. In a standard 96-well plate width 3 can be approximately 4.5 mm. When a single pipette tip column is inserted through the modified plate, one function of the plate modifier is to keep the pipette tip column and pipette vertical when positioned in the plate so that the combination of pipette, pipette tip column and plate is stable and does not tip. The diameter hole (width 3) in the plate adapter is compatible with the pipette tip column inserted into the plate.

An added benefit of using the adapter is that it can center the column in the well of the plate and in some cases, keep the column end from sealing at the plate well bottom by preventing the lower end column from settling completely into the plate. With a precise and accurate fitting of the column diameter with the diameter of the plate hole (width 3), the end of the column can be positioned to just above the bottom of the plate well, thus preventing the end of the column from being sealed at the well bottom.

The single channel adapter can also be used with a tube or vial. The tube or vial can be placed in a rack or other holding apparatus.

Two or more adapters may be used to secure a multichannel pipette. It may not be necessary to employ an adapter in each well as long as two or more adapters are placed far enough apart to position all columns attached to the multichannel pipette similarly.

Figure 3B:

FIGS. 3A and 3B show a plate adapter that modifies all 96 holes of the plate. Any configuration can be used to fit the modifier to the plate. In the embodiment depicted in FIGS. 3A and 3B, the adapter has protrusions that fit in the wells of the plate, keeping the adapter positioned on the plate. Other embodiments may just have one or two protrusions to keep the adapter positioned. Other embodiments may keep the adapter positioned without any protrusions but may use an outside ridge that fits around the outside top of the plate. In the embodiment shown in FIG. 3A, the hole in which the column is inserted is knurled, serrated or notched with saw-like ridges. This is to prevent sealing of the pipette tip column with the well of the plate. Sealing of the plate well with the column may be detrimental to liquid flow. Other embodiments of preventing well sealing with the column include: appropriate holes in the plate adapter or serrations or ribbing on the pipette tip column itself. Other embodiments include any mismatch of air sealing components such as sealing of the plate adapter protrusion with the 96 well opening. The adaptor can also be formed as a strip to fit into 2 or more wells or a partial plate, e.g. 24 wells of a 96-well plate.

Although FIGS. 2A-2B and 3A-3B depict portable adaptors, the adaptors can instead be incorporated into the plate or the column. In these embodiments, the plate or column would likely be custom manufactured especially for this apparatus.

It was discovered that supporting the plate or having a larger base support at the bottom of the plate also improved stability. Adding or securing a base to the 96 well plate increased surface area of the plate, and the pipette with pipette tip columns was less likely to tip over. Increasing the area of the plate by at least 50%, 100% 200% up to 500% increased the stability of the pipette and pipette tip columns. However this was not enough to provide a secure system that did not tip over.

An adaptor or modifier can be used on top of the microplate to adjust the diameter of the wells. In some cases, the diameter of the pipette tip columns is small relative to the wells of the deep-well plate. In some embodiments, a plate adaptor or modifier can be placed on the deep-well plate or the pipette tip column that effectively narrows the diameter of the wells within the deep well plate. The attachment may also center the column in the well. This narrowing of the well diameter prevents the bottom of the pipette tip column from reaching and sealing at the bottom of the deep well plate. The attachment can be on 1 well, several wells, or all 96 wells.

One embodiment of the attachment is shown in FIG. 1. This attachment effectively is part of the deep well plate. For the purpose of this invention, the definition of the deep well plate includes, if necessary, a top attachment to narrow the opening of the plate well holes relative to the tip column diameters to keep the pipette and pipette tip columns vertical. So all of this had to be tested to make certain the ends of the columns did not seal while still maintaining the pipette in a position that was 45 degrees or less to perpendicular. In some embodiments, the pipette is 35 degrees or less from perpendicular. For the purpose of this invention, the definition of vertical is 0-35 degrees from perpendicular. The attachment may cover the entire deep well plate or may be inserted on one or more column entering the deep well plate.

Use of the adaptor is not limited to deep-well plates. In some embodiments the microplate can be quite shallow, for example having a height of less than 2.2 cm, less than 2 cm, less than 1.5 cm, less than 1 cm or even less than 0.5 cm. The function of adaptor is to keep the standless pipette that is engaged with at least one pipette tip column, substantially vertical in the microplate, tube or vial.

Once balance and stability is achieved, it does not matter if one column or several columns are balanced. If more than one column is being balanced, but not all of the channels of the pipette are used, more secure balancing can be achieved by spreading the columns out across the multi-channel pipette. The system of pipette and pipette tip column can support 1 column, 1-8 columns 1-12 columns or 1-24 columns with the appropriate pipette. The pipette can be single-channel or multi-channel pipette.

Another technical problem was that it is very important to have the lower end of the pipette tip column very near the bottom of the well in the vial or plate without sealing the open lower end of the column. Otherwise, the ability to pick up of small volumes of liquid and pump them into the column would be inconsistent or impossible. The stand and liquid robotic handlers are designed and programmed to keep the tip of the column from touching the bottom and sealing. In fact, it is very easy to seal the bottom of the column and care must be taken not to do so.

The problem of sealing can be solved by carefully selecting the deep-well plate geometry to accommodate the column in the well. One solution is to select the shape of the well bottom so that a seal could not readily be formed. In one embodiment, a diamond-shaped well bottom was used so that the round column tip could not seal on the well bottom. This configuration was found to allow the pickup of small drops of liquid. In fact, any irregular shape at the well bottom can be used to prevent sealing of the lower end of column, as long as the shape does not prevent complete aspiration of small liquid volumes.

The distance between the lower end of the pipette tip column and the well bottom can be particularly crucial when pipetting small volumes. The lower end of the pipette tip column can even be touching the well bottom as long as a seal is not formed. If larger volumes are aspirated and expelled, the distance between the lower end of the pipette tip column and the well bottom can be greater.

Another solution to the sealing problem is to select the combination of microplate and column in such a way that the column is positioned at the appropriate height. This can be accomplished by selecting the diameter of the column so that a friction fit or restriction of the column prevents the column from sealing on the bottom. However, the danger is that a seal could possibly be formed around the sides of the column in the deep-well chamber. Sealing of the chamber could cause development of a pressure (during the expel step) or vacuum (during the aspirate step) and disrupt fluid flow in and out of the column. This design had to be examined to determine if a detrimental seal around the column would be formed.

Another potential problem is that it could be difficult to remove the pipette tip columns from the plate if a seal were formed. So all of these potential problems were to be tested to make certain the ends of the columns did not seal while still maintaining the pipette in a position that was 45 degrees or less from perpendicular. In some embodiments, the pipette is 35 degrees or less from perpendicular.

It was also necessary to confirm that the working standless electronic pipette system with pipette tip column would produce a useable, pure extraction product. Pipette tips are not usually completely immersed in the liquids being transferred. In addition to the sealing issue, contamination could result from liquids covering the outside of the tip. It was unknown whether this issue would negatively impact the purity of the extracted analyte. The results of the testing after the complete apparatus was built, described in Example 1, show that it is possible to effectively purify protein with the columns immersed in sample and wash solutions.

In certain embodiments, the deep well plate can be secured to the work surface or to a base. In these embodiments, it is less critical that the pipette be completely vertical i.e. perpendicular to the deep well plate. Instead, the pipette can be in the range of between 1 degree and 45 degrees from perpendicular (vertical). Because the plate is secured, the pipette with pipette tip columns will not fall over. An advantage of positioning the pipette and columns at an angle is that the columns would not seal as easily against the bottom of the plate.

Any means can be used to secure the plate. When the plate is secured to a base, the base can be made of any "hard" materials including plastic, metal or a combination. The base should have sufficient area to keep the microplate from falling over when a pipette and tip(s) are inserted into the plate. The base can accommodate one or more microplates.

Figures 4A, 4B:
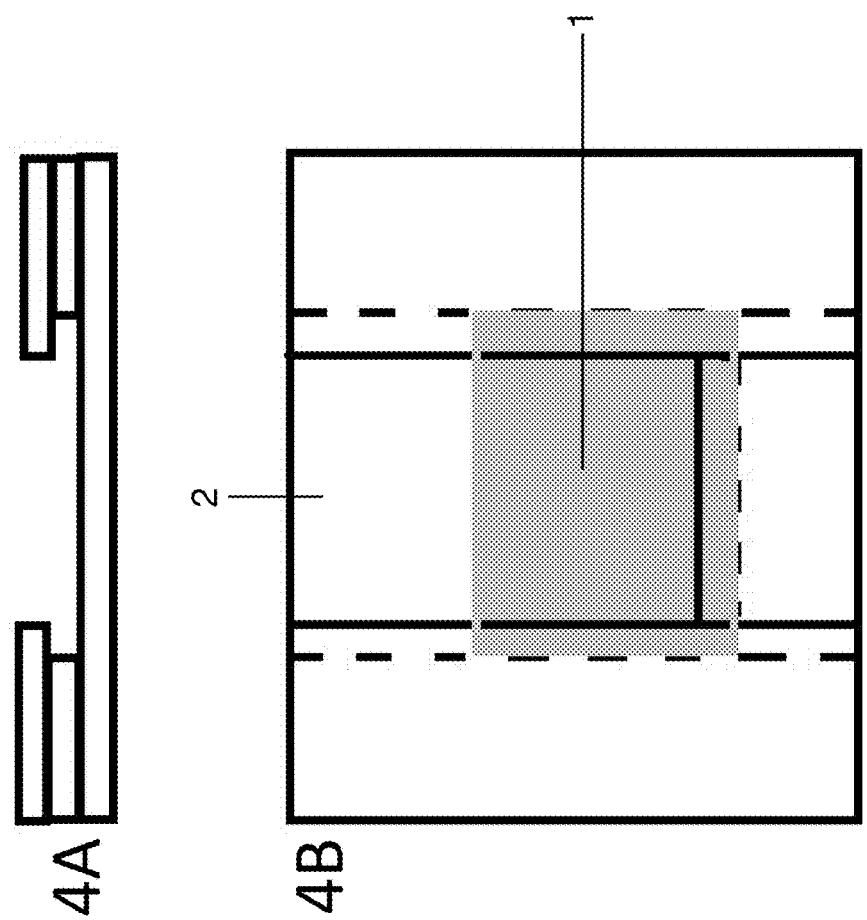
FIG. 4A is a side view and FIG. 4B is a top-down view of an embodiment of a base that can be used with the invention.

An embodiment of such a base is shown in FIGS. 4A and 4B. When an SBS style microplate is used, it can slide into a base and be held down on multiple sides by a lip as depicted in FIG. 4A. The base in this embodiment is comprised of 3 sheets of material, e.g. plastic. The sheets are configured to add an overhang or lip under which the base of the microplate can be secured. In this embodiment microplate 1 slides onto the base from open end 2 and the lip "grabs" the microplate (FIG. 4B). In this embodiment, the lip can extrude e.g. 1-3 mm to the center and 1-3 mm in height above the base. FIG. 4B shows the position of microplate 1 in a top down view of the base. All components of the base are fixed.

Another method of securing the plate is to have sliding pieces that move into place to hold the deep well block down. This embodiment can accommodate either SBS or ANSI format plates. For example, the microplate can be placed in the center of a base and plastic or metal pieces on runners or slides can slide toward the block and secure it with a friction fit. A third embodiment would be to have clamps on multiple sides that swivel toward the deep well block to provide a friction fit. This embodiment can be used with SBS or ANSI plate formats.

Pipette Firmware and Firmware Control

Electronic pipettes have a self-contained firmware that allows programming of the pipette to perform pipetting and mixing operations. The firmware includes the programs and data structures that internally control the pipette. Because of space and memory limitations, the programming is directed to the operations for which a pipette is intended e.g. pipetting (aspirating, expelling), transferring and mixing liquids.

The use of a pipette as a pump for pipette tip columns involves operations far more involved, complex and different from pipetting. This operations include slow control of the flow rate, pumping delays, control of the number of back and forth flow cycles, pump displacement volume, control of the blow out function e.g. not have a blow out or have a controlled blow out between capture and wash and between wash and elute, be able to change the plunger aspiration volumes in for each step of extraction, capture, wash and elute, be able to add additional captures, washes, and elutions, and other functions if necessary. (Pipette blow out is the pipetting function where during expulsion, the piston of the pipette travels past the zero position pushing the last bit of liquid out of the pipette tip.) The pipette should also be able to direct or signal the user the step in the extraction process because the pipette must be moved manually from well to well containing the various capture, wash and elution liquids.

This operational control is not available or programmable on commercial pipettes. The invention of a freestanding electronic pipette required redesigning the firmware and the procedure used to program the pipette for use. The handheld electronic pipette software is not compatible with the pipette tip column operation and at the outset, it was not known whether an electronic pipette could be redesigned. The following technical challenges were addressed and solved in the instant invention.

It was not known whether the pipette had enough buttons for the necessary programming.

It was not known whether the display would be compatible.

It was not known whether the proper functions could be identified by the display and use of buttons.

It was not known whether the microprocessor was compatible with the type of firmware that had to be designed.

It was not known whether there was enough memory to operate the pipette in a self-contained extraction mode with multiple steps.

It was not known whether the plunger speed and position control were sufficient for extraction.

Examples of the number and types of steps required for pipette tip column operation are outlined in the Examples that follow. The steps and operations are much more complex than normal pipetting operations. In some cases, the plunger movement must be greater than the amount of liquid picked up and moved back and forth through the column. The programming must accommodate this when necessary. Firmware may have to be modified to prevent a blow out at the end of the expel cycle (except at the final expel for elution.) It would not be obvious to use an off the shelf electronic pipette because it would not work for pipette tip columns. Nor would it be obvious that a pipette with limited electronic capability could be modified as a free-standing apparatus used with columns and a deep-well plate.

The details the firmware design used to meet the goals of operating a pipette tip column are given in the various examples herein. For some types of columns, it is necessary to program extra aspiration and expulsion volumes. For some types of high back pressure columns, a delay at the end of each half cycle may be needed. If the back pressure of the column is low enough, then the delay at the end of each half cycle may not be needed. The flow rates can be less than what is used in normal pipetting operations. In some cases, the flow rates are up to 50 times slower than what is used in normal pipetting operations.

The Columns

A pipette tip column is defined herein as any column adapted to engage the barrel of a pipette either directly or indirectly. The invention can be used with any type of pipette tip column that uses pipette pressure to force liquid in and out of the column bed from the bottom of the column. The pipette tip column body can be a commercially-available pipette tip, a modified tip or it can be a custom column body, tube, syringe or similar materials. Any volume of pipette tip can be used. For example the pipette tip volume can be 1 µl, 50, 10 µl, 20 µl, 50 µl, 100 µl, 200 µl, 500 µl, 1000 µl, 5 ml, 10 ml, 20 ml, 25 ml or more.

Examples of pipette tip column contents are a packed resin bed, disk, precipitated bed, monolith, media encapsulated in a fiber or polymer or a fluidized bed. Column resins include affinity resins, reverse phase, normal phase, hydrophobic interaction phase, ion exchange, silica, polymer, inorganic phases and others.

The bed can be positioned between two frits using a packing method in which pressure is not used to compact the bed. In certain embodiments, the columns of the invention do not have significant bed compression. With bed compression, beads are deformed which causes them to fill the interstitial space. Column beds can be compressed with a force to pack the column into the column space. This force can be applied with vacuum or pressure of liquid containing the packing beads for physical compression of the beads into the column chamber. With columns of the invention, the beads are not pressed together to form flow constrictions or dead end flow spaces.

The volume packing density of the bed can be measured as a ratio of the volume of beads without having any direct contact causing the deformation of the bead divided by the volume of same amount of beads where the bed has been compressed. As the volume column is decreased for the same amount of beads the volume packing density increases. A bed that has been compressed 10% has a volume packing density of 1.00/0.90 which equals 1.11. A bed that has been compressed 20% has a volume packing density of 1.00/0.80 which equals 1.25. A bed that has not been compressed is 1.00/1.00 which equals 1.00. Columns of the invention that contain compressible beads have a volume packing density within the range of 1.00 to 1.05.

In other embodiments, the columns are comprised of a more compressed packed bed of medium. For example, a packed bed of medium might be used for enrichment columns in which cells pass through but contaminants are captured.

Affinity resins have a gel like, hydrophilic structure that swells in the presence of water or polar solvents. The swollen polymers contain pore that allow solvent to diffuse in and out of the resin bead. The swelling can be significant. For example a cellulose, agarose or Sepharose substrate will swell 5-10 times its original size when contacted with water. In the swelling process pores are opened up producing beads with a pore diameter up to 500 Angstroms and larger allowing bio molecules to migrate and diffuse into the bead along with the solvent.

In some embodiments of the invention, a polymer substrate is used that does not swell upon exposure to water. In substrates which do not swell in water (solvent), buffer molecules, biomolecules and/or cells cannot enter pore in the substrate. The substrate may be polystyrene, polyacrylate type, poly ester, other olefin polymer, other polymer, or inorganic substrate material. Inorganic polymers include polysiloxane and polyphosphazene, silicone, etc. Inorganic materials include aluminum oxide, zirconia, silica, etc. Organic polymers include low density polyethylene (LDPE), high density polyethylene (HDPE), polypropylene (PP), polyvinyl chloride (PVC), polystyrene (PS, nylon, nylon 6, nylon 6,6, Teflon (Polytetrafluoroethylene), thermoplastic polyurethanes (TPU), polytetrafluoroethylene (PTFE), polychlorotrifluoroethylene (PCTFE) and other polymers. When exposed to water the particle size increase of these substrates are less than 5%, 4%, 3%, 2%, and 1%. Swelling may be controlled by controlling the polarity of the interior of the substrate to be nonpolar or non-hydrophilic. Water is limited in entering the interior of the bead and hydrating the bead.

It some embodiments, an impervious resin is used. The use of an impervious resin can be an advantageous for capturing cells because they are large and in many cases, they cannot enter resin bead pores. Most prokaryotic cells range in size from 0.2 to 5.0 µm in diameter and most eukaryotic cells range in size from 1.0 to 100 µm in diameter. The reduction in non-usable surface area will decrease reagent costs as the capacity of the column is decreased. The use of a resin with the rigid structure will also facilitate easier column packing procedures.

The columns can be sterilized. For example, water swollen gels and other column media may be sterilized. Impervious organic and inorganic column materials may be sterilized. Substrates based on silica and other inorganic materials may be sterilized.

Column Frits

In certain embodiments of the invention, one or more frits are used to contain the bed of medium within a column. In some embodiments, only a bottom frit is used and a bed of medium is positioned above the bottom frit. In other embodiments, an upper frit and a lower frit are utilized. The frits of the invention are porous, since it is necessary for fluid to be able to pass through the frit.

For samples containing cells, the frit pore size should be large enough to prevent plugging with cells or cell debris. It is important that the frit does not provide dead-end or restricted-end flow paths that could potentially trap or damage cells. It is desirable that the frit have little or no affinity for liquids or cells with which it will come into contact during the column use.

In certain embodiments, one frit (e.g., a lower, or bottom, frit) extends across the open channel of the column body. Often, the bottom frit is attached at or near the open lower end of the column. A bed of separation medium is positioned inside the open channel and in contact with the bottom frit. In many embodiments, a top frit is employed, however it is not mandatory. In certain embodiments, there is a gap between the bed of medium and the top frit. This gap is referred to as a bed-frit gap.

Frits of various pores sizes and pore densities may be used provided the free flow of liquid is possible and the solid phase is held in place. However, the frits must have specific porosity characteristics. It is not only a matter of having sufficiently large pores. The pore shape is important as well. Pores cannot be destructive or restrictive to cells.

Frits of the invention preferably have pore openings or mesh openings of a size in the range of about 5-500 µm. In certain embodiments, the pore size is in the range of 10-200 µm, 33-150 µm, e.g., about 33-43 µm. Frit pore sizes of 20, 33, 37 and 43 um pore size are acceptable. Of course, increasing the frit pore size can only be done if the packing material retained.

The frits of the invention can be made from any material that has the required physical properties as described herein. Examples of suitable materials include polymers, fiber, fabric, plastic (including sintered plastic), nylon, polyester, polyamide, polycarbonate, cellulose, polyethylene, nitrocellulose, cellulose acetate, polyvinylidine difluoride, polytetrafluoroethylene (PTFE), polypropylene, polysulfone, PEEK, PVC, metal and glass. However, any suitable material that meets the above functional requirements can be used for the frit.

Certain embodiments of the invention employ a membrane screen as the frit. The use of membrane screens can provide low resistance to flow and hence better flow rates, reduced back pressure and minimal distortion of the bed of medium. The membrane can be a woven or non-woven mesh of fibers that may be a mesh weave, a random orientated mat of fibers i.e. a "polymer paper", a spun bonded mesh, an etched or "pore drilled" paper or membrane such as nuclear track etched membrane or an electrolytic mesh.

Some embodiments of the invention employ a relatively thin frit. The frit or frits should be sufficiently thin such that cells will not become trapped or die within the frit during column operation. In most embodiments, the frit thickness is less than 10,000 µm, less than 8000 µm, less than 6000 µm or less than 4000 µm (e.g., in the range of 20-4000 µm, 40-2000 µm, or 50-350 µm). In certain embodiments, the frits are less than 200 µm thick (e.g., in the range of 20-200 µm, 40-200 µm, or 50-200 µm), or less than 100 µm in thickness (e.g., in the range of 20-100 µm, 40-100 µm, or 50-100 µm). However, thicker frits can also be used in some embodiments, frits up to 1 mm, 2 mm, 3 mm, 4 mm, 5 mm and even 6 mm thick may be used if the pore size of the frit can be increased dramatically.

The frit can be attached to the column body by any means which results in a stable attachment. For example, the screen can be attached to the column body through press fit, friction fit, contained with a collar, welding or gluing.

In certain embodiments, the column frits may be cut from sheets of porous frit material. These frits can be made up of sintered polymer, porous polymer, organic material or metal. The porous sheet frit may be 0.25, 0.5, 1, 1.5, 1.59, 2, 2.5, 3, 3.2, 3.5, 4, 5, 6, 8, 10 mm thick, or 1/32, 1/16, 3/32, 1/8, 3/16, 1/4, inch thick. The frit pore diameter can be in the range of 10, 20, 30, 40, 50, 60, 70, 80, 90, 100, 120, 140, 160, 200, 300, 500, 800 micron.

The Sample

The apparatus and methods of the invention can be used to extract a variety of analytes including nucleic acids (DNA including plasmid DNA, genomic DNA and RNA), proteins, polypeptides, drugs, organic molecules, and inorganic molecules and other materials and molecules. In some embodiments, cells are isolated from biological samples. In these embodiments the isolated cells can be viable.

Cells are defined herein as membrane-bound structures that occur as functional units of life (such as in unicellular organisms, e.g. bacteria, protozoa, etc.), or as structural or fundamental units in a biological tissue specialized to perform a particular function in multicellular organisms (e.g. plants and animals). Self-replication is not a necessary property of cells as defined herein; the definition includes entities such as viruses, parasites and exosomes.

For example, cells can be captured from biological fluids such as blood, urine, saliva, spinal fluid or semen, tissues such as brain or tumor tissue and other samples such as fecal (stool) or hair. In certain embodiments, sample preparation steps are performed prior to the isolation of cells on a column. For example, when cells are captured from blood, the blood can be fractionated by centrifugation and only the buffy coat loaded on the column. Alternatively, whole blood can be diluted or loaded directly on the column. In certain embodiments, the devices and methods can be used for the analysis of cells from crime scene samples.

In some samples, cells are free and exist individually in solution. There are other samples, such as tissues in which cells are aggregated or form cell-cell adhesions. In addition there are cells that start off as tissues but then slough off to form free cells. Circulating tumor cells for example exist in blood and may form an adhesion to other places in the body. Sample preparation techniques exist that can mechanically or chemically disrupt and dissociate cells in order to form single cell suspensions. These methods are gentle and in wide use. Kits are available that use enzymatic digestion in combination with mechanical disruption and the option of heat. There are products available from Miltenyi Biotec and Roche Life Sciences for example.

Cells isolated using methods and devices of the invention are not limited to a particular cell type; cells captured by the methods of the invention can be eukaryotic or prokaryotic cells. Eukaryotic cells can be from protozoa, chromists, plants, fungi or animals such as mammals, amphibians, birds, fish, reptiles and invertebrates.

Cells can be engineered or wild type. For example, T cells have been engineered to produce antibodies that bind cancerous cells (Grupp et al., N Engl J Med. 2013 Apr. 18; 368(16):1509-18). These engineered T cells were introduced into patients with leukemia to achieve remission or tumor size reduction. In this type of application, patients' T cells could be isolated using a column of the invention, engineered and then proliferated in cell culture. After the engineered T cells were grown, they could be isolated with a sterile column prior to introduction into a patient.

Stem cells and other cell types may be captured, purified with packed bed column technology in an open system or a sealed system and then manipulated using CRISPR type genome editing methodologies and technologies. The cells may be collected for further downstream processing.

A non-limiting list of cells that can be isolated by the columns of the invention includes epithelial cells, hormone secreting cells, sensory transducer cells, neuron cells, glial cells, lens cells, metabolic cells, storage cells, barrier function cells such as lung, gut, exocrine glands and urogenital tract, kidney cells, extracellular matrix cells, contractile cells, blood and immune system cells, germ cells, nurse cells, interstitial cells, activated B-cells, mature B-cells, cytotoxic T-cells, helper T-cells, activated T-cells, natural killer (NK) cell, monocyte and macrophage, activated macrophage, endothelial cell, smooth muscle cell, dendritic cell, mast cell, fibroblast (stromal), epithelial cell, adipocyte, stem cells, granulocytes, platelets, erythrocytes circulating tumor cells, Alexander cells, astroglia, B Lymphoblast, B Lymphocyte, basophil, cortical neurons, cutaneous T cells, lymphocytes, embryonic cells, enterocytes, epithelial cells, transformed cells, immortalized cells, large T antigen, epithelial neuroendocrine, erythroblast, fetal, fibroblast, glial cell, glioblastoma, Hela cells, histocyte, human papillomavirus, hybridoma: e.g., helper T lymphocyte, keratinocyte, killer cell, large cell, lymphoblast, lymphoblast B lymphocyte, lymphoblast Human Immunodeficiency Virus, lymphocyte, medulloblastoma, megakaryoblast, melanocyte, melanoma, monoblast, myeloblast, neuroblast, neuroendocrine, osteoblast, pluripotent stem cell, pre-B lymphoblast, promyeloblast, retinoblastoma, Schwann cell, squamous cell, T lymphoblast, T lymphocyte, T-cell.

Cells isolated can be from any tissue. A non-limiting list of tissue type examples follows. lung, ascites, bone marrow, bone, brain, cervix, colon, connective tissue, duodenum, eye, kidney: skin, kidney, liver, lung, lung: pleural effusion, mammary gland, ovary: ascites, ovary, pancreas: lymph node, pancreas, peripheral blood, pharynx, placenta, prostate, retinal pigmented epithelium, skin, spleen, stomach: derived from metastatic pleural effusion, stomach, submaxillary salivary gland, testes, thyroid, tongue, urinary bladder, uterus, adrenal gland, airway epithelium, aorta, bladder, blood, bone marrow, brain, breast, breast derived from metastatic site: pleural fluid, bronchiole, bronchus, carcinoma, cecum, cord blood, cornea, ectocervix, embryo, embryonic kidney, endocervix, endometrium, epithelium, esophagus, eye, fetus, foreskin, gingival biopsy, heteromyeloma, intestine, kidney, lung adenocarcinoma, lymph node, lymph node derived from metastatic site: peritoneal effusion, mammary gland, marrow, mesencephalon, mesothelium, muscle, nasal septum, nervous, palatal, palatal mesenchyme, pancreas, peripheral blood, peritoneal effusion, peritoneum, peritonial effusion, pharynx: derived from metastatic site: pleural effusion, pleura, prostate, rectum, retina, retroperitoneal embryonal tumor, retroperitoneum, skin: derived from metastatic axillary node, skin: derived from metastasis on skin of thigh, small intestine, somatic cell hybrid, stomach, submaxillary, synovium, testis, thymus, thyroid, tonsil, trachea, trunk, umbilical vein, ureter, uterine, vagina, vascular, vein, vertebral epitheloid carcinoma and vulva.

Cells of a particular organ type or part of the body can be loaded onto a column. These include cells from the heart, liver, kidney, bone marrow, gut or from a spectrum of human tissues, including the circulatory, endocrine, gastrointestinal, immune, integumentary, musculoskeletal, nervous, reproductive, respiratory, urinary systems and other types. The cells may be from a specific individual or from the general population. Columns with these cells may be operated alone or in concert with other columns containing cells from other organs or biological systems. The columns can be operated in the chromatographic system in parallel or in series to mimic biological functions. Reagents can be introduced into the columns to determine the interaction of the reagents and the effect on the cells or to study or use the cells as organs.

Capture and Elution Strategies

This apparatus and method can be used for different extraction methods including but not limited to Protein A, Protein G, Protein L or other antibody extractions, IMAC and similar resins for recombinant tagged molecules, anti-Flag, Streptavidin, Avidin, reverse phase and ion pairing, reverse phase silica and polymeric normal phase, ion exchange and any resin that can be used in an extraction mode.

For methods involving cell capture, various mechanisms can be used for cell capture on the medium. Non-limiting examples include a functional group that has affinity for the cells, use of a tagged antibody, ion exchange, a tagged aptamer and an antibody loaded resin (Pro A, G etc.) covalent bonded linkers (alkyl thio, etc.), hydrogen bonded linkers. In some embodiments, a biotinylated antibody binds a cell surface marker and cells are isolated using a streptavidin resin. In certain embodiments, the resin can be comprised of an antibody. Other capture mechanisms such as hydrophobic interaction, reverse phase, normal phase, ion pairing and ion exchange can also be used.

Antibodies or other ligands used with the invention can bind cell surface markers. There are many commercially-available antibodies that bind cells. The following is a non-limiting list of human cell surface markers that can be identified by PCR.

B-Cell Surface Markers:

Activated B-cells: CD28, CD38, CD69, CD80, CD83, CD86, DPP4, FCER2, IL2RA, TNFRSF8, CD70 (TNFSF7).

Mature B-cells: CD19, CD22, CD24, CD37, CD40, CD72, CD74, CD79A, CD79B, CR2, IL1R2, ITGA2, ITGA3, MS4A1, ST6GAL1.

Other B-cell Surface Markers: CD1C, CHST10, HLA-A, HLA-DRA, NT5E.
T-Cell Surface Markers:
Cytotoxic T-cells: CD8A, CD8B.
Helper T-cells: CD4.
Activated T-cells: ALCAM, CD2, CD38, CD40LG, CD69, CD83, CD96, CTLA4, DPP4, HLA-DRA, IL12RB1, IL2RA, ITGA1, TNFRSF4, TNFRSF8, CD70 (TNFSF7).
Other T-cell Surface Markers: CD160, CD28, CD37, CD3D, CD3G, CD247, CD5, CD6, CD7, FAS, KLRB1, KLRD1, NT5E, ST6GAL1.
Natural Killer (NK) cell Surface Markers: CD2, CD244, CD247, CD7, CD96, CHST10, IL12RB1, KLRB1, KLRC1, KLRD1, NCAM1.
Monocyte and Macrophage Cell Surface Markers:
Activated Macrophages: CD69, ENG, FCER2, IL2RA.
Other Monocyte and Macrophage Surface Markers: C5AR1, CD163, CD40, CD63, CD74, CD86, CHST10, CSF1R, DPP4, FCGR1A, HLA-DRA, ICAM2, IL1R2, ITGA1, ITGA2, S100A8, TNFRSF8, CD70 (TNFSF7).
Endothelial cell Surface Markers: ENG, ICAM2, NOS3, PECAM1, SELP, TEK, VCAM1, VWF.
Smooth Muscle cell Surface Markers: MYH10, MYH9, MYOCD.
Dendritic cell Surface Markers: CD1A, CD209, CD40, CD83, CD86, CR2, FCER2.
Mast cell Surface Markers: C5AR1, FCER1A, FCER2, TPSAB1.
Fibroblast (Stromal) Surface Markers: ALCAM, COL1A1, COL1A2.
Epithelial cell Surface Markers: CD1D, KRT18, KRT5, KRT8, EPCAM.
Adipocyte Surface Markers: RETN.

One elution strategy involves competition. Cells are captured with a ligand that binds a cell surface marker and then eluted with the same ligand. In another example, cells bound to antibodies captured on ProA resin can be eluted with ProA, IgG or another molecule. Alternatively, the ligand could be bound to a tag which in turn, binds an antibody.

Another competition strategy utilizes ANTI-FLAG resin. A FLAG-labeled Fab or antibody that binds a cell surface marker could be engineered e.g., in *E. coli*. Many other types of functional groups can be used for competitive, equilibrium type reactions to capture and optionally elute and recover cells.

Alternatively, cells can be eluted by a physical change such as a change in pH or temperature. Preferably, an eluent can be selected that does not harm the cells, particularly when the recovery of viable cells is desired. In one example, a temperature-sensitive ProA resin can be used such as Byzen Pro resin made by Nomadic Bio Science. Using this type of resin, cells can be eluted at neutral pH by increasing the temperature as shown. In a second example, cells can be captured by antibodies specific to cell surface markers and eluted using a low-pH eluent. In this example, the elution step could be performed rapidly followed by a quick transfer of the purified cells to a neutral-pH solution.

A variety of affinity strategies can be used to capture cells on the column. However, it is also possible to use ion exchange. In alternate embodiments, cell capture may not be desired. Gel filtration (size-exclusion) or affinity chromatography can be used to enrich a particular cell type by separating cells away from non-cell components or by separating cells from each other based on their size. For example, circulating tumor cells (CTCs) are larger than other cell types and can be separated from other cells using size exclusion chromatography. Gel filtration could also be used to clean up a sample, e.g. a diagnostic sample. Non-cell material could be removed or taken up by the column.

In some embodiments, cells captured on a column can be eluted using enzymatic cleavage. For example, cells could be captured using ProA resin charged with antibodies that bind a cell surface marker. The antibody could then be cleaved with an enzyme such as papain or pepsin to elute the cells.

The columns and methods of the invention can be used to capture and elute viable healthy cells or diseased cells. In certain embodiments, cells can be captured using an aptamer specific to a cell surface marker. Aptamers can be single- or double-stranded RNA or DNA oligonucleotides. Aptamer sequences can be determined using Systematic Evolution of Ligands by Exponential Enrichment (SELEX) or other selection processes (see for example Base Pair BioTechnologies, Inc., Houston, Tex.). The aptamers can contain non-standard or modified bases. As used herein, a "modified base" may include a relatively simple modification to a natural nucleic acid residue, which confers a change in the physical properties of the nucleic acid residue. Such modifications include, but are not limited to, modifications at the 5-position of pyrimidines, substitution with hydrophobic groups, e.g., benzyl, iso-butyl, indole, or napthylmethyl, or substitution with hydrophilic groups, e.g., quaternary amine or guanidinium, or more "neutral" groups, e.g., imidazole and the like. Additional modifications may be present in the ribose ring, e.g., 2'-position, such as 2'-amino (2'-NH$_2$) and 2'-fluoro (2'-F), or the phosphodiester backbone, e.g., phosphorothioates or methyl phosphonates.

Aptamers can be chemically conjugated to chromatographic beads. For example, see Zhou et al., Trends in Analytical Chemistry. 2012 41:46-57. Alternatively, biotin-labeled aptamers could bind streptavidin resin. Cell elution can be performed by a means with disrupts the aptamer or the aptamer-cell bond. For example, RNase could be used to perform elution from an RNA-based aptamer. Other elution strategies that can be employed with aptamers are anti-sense, photocleavage (at an appropriate wavelength), use of an enzyme, heat, denaturing solution or chemical cleavage. An aptamer comprised of a disulfide bond could be treated with a reducing agent to disrupt the bond and release a bound cell. An aptamer containing a magnesium-dependent fold could unfold and release a bound cell with the addition of a chelator.

As described above, cell surface markers can be used to capture the cells. Elution of the cell can be accomplished using a strategy directed toward release of the capture marker without disrupting any of the other markers.

Sterile Processing

For some methods, it is desirable to process the sample under sterile conditions. For example, when the sample contains cells, the column and environment for processing, including capture, recovery, or contaminant removal (enrichment) may be sterile. As a result, it is possible to purify sterile cells. This can be accomplished by having the well containing the sample and buffers having a sealable interface between well containing sample and reagents and the end of the column as it is placed into the well to process the material contained within the well. The preferred sealing is a silicone opening that opens as the column is inserted into the well.

The silicone conforms around the column end forming a seal to maintain sterility. The silicone opening re-closes when the column end is removed. The well is self-sealing with removal of column end. Other possible column well sealers include metal, such as aluminum, rubber or plastic that may be pierced or opened as the lower end of the column is inserted into the well.

The well may allow sterile air to enter and escape to allow back and forth of fluid from the well chamber in and out of the column. In another embodiment, the well may collapse with back and forth flow. This can be accomplished by placing a collapsible bag within the well chamber.

With these tools and method sterility of the column, inside column hardware, and reagents is maintained.

Use of Instrument in a Laminar Hood without a Computer Physical Connection

In some embodiments, the electronic control of the back and forth flow pipette or syringe was fully contained in the free standing instrument. In some embodiments control of the instrument was partially through a microprocessor contained within the instrument and partially or fully controlled with a computer connected to the instrument by wireless control. The back and forth flow free standing column instrument may be used in a laminar hood without computer wires coming out of the hood connecting to a computer.

Having now generally described the invention, the same will be more readily understood through reference to the following examples, which are provided by way of illustration, and are not intended to be limiting of the present invention, unless so specified.

EXAMPLES

Example 1

General Operation and Use of the System with a Step-by-Step Operation of a 5 μL Protein G Resin Bed in 200 μL Pipette Tip Column Body 1) Set up 2 ml deep-well plate with capture, wash and elution solution in rows.
2) Program firmware on pipette.
   Set the volume for conditioning buffer to 180 μL.
   Set the volume for capture to 180 μL.
   Set wash to two sets at 180 μL each.
   To elute 10 or 15 μL, set the elution volume to 50 or 55 μL. (In this procedure, extra volume is added to the elution aspirate and expel volumes to ensure that all the liquid is taken up and expelled. This can be necessary to overcome the positive pressure created above the bed of the column when the column is engaged with the pipette.)
3) Start program
4) Attach pipette tip columns
5) Attach centering cylinder to the two end columns or optionally fix a column centering cover to the top of the deep-well plate.
6) Submerge into 200 μL conditioning solution in deep-well plate and start conditioning. The column will condition with back and forth flow at specified flow rate and number of cycles. A cycle is comprised of a single aspirate step followed by a single expulsion step. When cycling is finished, the pipette will signal completion.
7) Submerge the pipette tip columns into the 200 μL sample solution in the deep-well plate and start pipette operation. Column will capture with back and forth flow at specified flow rate and number of cycles. When cycling is finished the pipette will signal completion.
8) In similar manner, perform 2 cycles in 200 μL Wash 1.
9) In similar manner, perform 2 cycles in 200 μL Wash 2.
10) Perform elution in similar manner.
    a) For a 10 μL elution, the pipette is programmed to 50 μL aspiration and expulsion for 4 cycles. The final material is blown out after the last cycle.
    b) For a 15 μL elution, the pipette is programmed to 55 μL aspiration and expulsion for 4 cycles. The final material is blown out after the last cycle.
11) The column may be eluted in a second volume of elution solvent.
12) The pH of eluted material may be adjusted if desired.

This is the step-by-step operation of 80 μL pipette tip 1000 uL body column filled with Protein A resin.

1) Set up 2 ml deep-well plate with capture, wash and elution solution in rows.
2) Program firmware on pipette.
   Set condition buffer to 480 μL.
   Set capture to 500 μL.
   Set wash to two sets at 500 μL each.
   Set elution to 50 μL or 55 μL as described above.
   Set the pause between pumping strokes to 20 seconds.
3) Start program
4) Attach pipette tip columns
6) Submerge the electronic pipette with pipette tip columns attached into 500 ul conditioning solution in the deep-well plate and start the conditioning step. The column will condition with back and forth flow at specified flow rate and number of cycles. When cycling is finished, the pipette will signal completion.
7) Submerge the pipette tip column into the 500 μL sample in plate and start pipette operation. Column will capture with back and forth flow at specified flow rate and number of cycles. When cycling is finished the pipette will signal completion.
8) In similar manner, perform 2 cycles in 500 μL Wash 1.
9) In similar manner, perform 2 cycles in 500 μL Wash 2.
10) Perform elution in similar manner.
    a) For a 200 μL elution, the pipette is programmed to 430 μL aspiration and expulsion for 4 cycles. The final material is blown out after the last cycle.
    b) For a 240 μL elution, the pipette is programmed to 470 μL aspiration and expulsion for 4 cycles. The final material is blown out after the last cycle.
11) The column may be eluted in a second volume of elution solvent.
12) The pH of eluted material may be adjusted if desired.

Example 2

Comparison Between the Standless Pipette, Spin Columns and Manual Handheld Pipette An experiment was performed comparing the technology of the invention with pipette tip columns used in a spin column mode and in a manual mode using a manual pipette. Pipette tip columns (PhyNexus, Inc.) were used in three different modes: (a) spin column/centrifuge, (b) manual pipette, and (c) standless electronic pipette. In each mode, an identical volume of the initial sample protein was purified by single-lots of IMAC, Protein G and Protein A pipette tip columns using identical wash and elution buffers. Protein samples consisted of either mouse IgG1, human IgG, His6-ubiquitin or His6-rubredoxin protein standards spiked into appropriate binding buffer processed using appropriate pipette tip columns containing Protein G, Protein A, or Ni-IMAC resin. Sample flow-through, wash flow-through and elution fractions were assessed for capture efficiency, purity and overall yield by quantitative HPLC analysis.

The pipette tip column used as a spin column in a centrifuge: Interaction between the sample and affinity resin in a pipette tip column when operated in spin column mode is limited to a single pass through the bed during the centrifugation step. Results obtained in this configuration exhibit the versatility of the pipette tip column format while at the same time demonstrating inherent limitations of the spin column process resulting from reduced contact between sample and resin. The purification efficiency for two His6-tagged proteins using Ni-IMAC pipette tip columns was measured and the purification efficiency of mouse IgG1 processed with Protein G and Protein A pipette tip columns was measured in all three methods.

The pipette tip column used in a hand-held manual pipette: Using a pipette to control the purification process allows increased contact with the resin by back and forth flow of the sample through the column. A manual pipette used with an identical column with same sample gave better capture and recovery of protein in a smaller volume compared to the spin mode. In general, results were as much as 65% better than those obtained when the pipette tip column was used as a spin column. Capture efficiency for two separate His6-tagged proteins using Ni-IMAC columns demonstrating reduced capture efficiency when samples are processed in the spin column mode. Capture efficiency is improved by increasing the number of capture cycles when processing pipette tip columns using a manual pipette. 4-6 cycles are normally adequate to capture the protein to equilibrium. However, it is very tedious holding the column and tip in the correct position throughout the pumping operations. If the column is held too high, some of the fluid in the vial or plate may not be pumped into the column. If the column is held too low, the end of the column may seal on the plate or vial and liquid may be prevented from flowing in or out of the column. The flow rate is also difficult to control using the manual pipette.

Pipette tip column used in a standless electronic pipette: An electronic pipette is used in a similar manner to the manual pipette but is free-standing with the columns contained in a deep-well plate. The electronic pipette firmware was modified so that it could be programmed to use precisely controlled back and forth flow rates, number of cycles, pause between capture and wash and between wash and elute while optionally adding more capture, wash and/or elution steps if needed. The piston position and aspiration and expulsion volumes were controlled relative to the volume of liquid passed through the column with controlled blow out at the end of the various operations. The standless electronic pipette used with the pipette tip column gave superior recovery and purity over the other two methods tested. The results were on average, 130% better than spin columns at sample capture and 70% better than sample capture using manual operation.

The capture efficiency of mouse IgG1 on 80 µL Protein G columns was determined keeping all conditions the same and comparing the percent captured with spin column, manual pipette and standless electronic pipette (Table 1).

TABLE 1

|  | % captured |
| --- | --- |
| Spin Column Method | 39 |
| Manual Operation, 2 cycles | 64 |
| Standless Electronic Pipette | 91 |

Table 2 shows results of the purification of two His-tagged proteins on IMAC resin keeping all conditions constant and comparing spin column and standless electronic pipette. The 500 µL samples consisted of either 0.9 µg His-rubredoxin in PBS buffer containing 0.05% Tween 20 or 5 µg His-ubiquitin in PBS buffer containing 0.05% Tween 20. The samples were processed by columns containing 80 µL of IMAC resin.

TABLE 2

|  | His-rubredoxin | His-Ubiquitin |
| --- | --- | --- |
| Spin Column Method | 82 | 92 |
| Standless Electronic Pipette | 89 | 97 |

Columns were equilibrated with 500 µL PBS buffer. 500 µL samples consisting of 5 µg mouse IgG1 in PBS buffer containing 0.05% Tween 20 was captured by one of three methods. The spin method was carried out by adding the sample to the top of the columns and inserting the column into a 15 mL conical tube. This sample was forced through the column by spinning in a clinical centrifuge at ~5K rpm for 30 seconds. For manual operation, the pipette was set to 480 µL and the plunger was depressed. The column was attached to the pipette while keeping the plunger depressed. The columns were submerged into the 500 µL sample keeping the pipette and column completely upright and the end of the column at the bottom of the sample. The plunger was released at the slow rate of 5 seconds to aspirate the full 480 µL. After aspiration, the pipette and column were held in the same position for 15 seconds. The plunger was next depressed at a rate of 5 seconds to completely dispense 480 µL. The pipette and column were held at the same position for 15 seconds. This consists of 1 cycle and the procedure was repeated for a second cycle. For standless Electronic Pipette operation, the manual method was repeated using the programming on the electronic pipette.

Table 3 shows the comparison of 5 µL and 80 µL bed volume columns of Protein A resin capturing and recovering human IgG with a manual pipette comparing 1, 2, 3, and 4 capture cycles. The sample consists of 200 or 500 µL for the 5- and 80-µL bed volume columns, respectively. Samples consist of 0.02 mg/mL human IgG (Sigma, 14506) in PBS buffer supplemented with 0.05% Tween 20. Aliquots were removed after each cycle and quantified by HPLC.

TABLE 3

|  | 5 ul Column | 80 ul Column |
| --- | --- | --- |
| 1 cycle | 15 | 42 |
| 2 cycles | 10 | 66 |
| 3 cycles | 22 | 78 |
| 4 cycles | 25 | 88 |

Table 4 compares the elution efficiency of mouse IgG1 from a 80 µL protein G resin column keeping everything the same with a spin column, manual pipette and standless electronic pipette. Columns were loaded as per Table 1 and washed with 500 µL PBS buffer followed by a second wash of 500 µL 140 mM NaCl. Columns were subjected to two elutions of 250 µL elution buffer, each, consisting of 200 mM sodium phosphate pH 2.5, 140 mM NaCl. Elutions were analyzed by quantitative HPLC.

TABLE 4

|  | Elution 1 (%) | Elution 2 (%) |
|---|---|---|
| spin | 18 | 19 |
| manual 4 cycles | 40 | 12 |
| Standless Electronic Pipette | 43 | 18 |

Table 5 compares the elution of proteins from a 5 uL IMAC column using a spin column and the standless electronic pipette. 200 μL samples consisted of either 0.012 mg/mL His-rubredoxin or 0.012 mg/mL His-ubiquitin. Samples were captured as described and washed twice with 200 μL 5 mM imidazole in PBS buffer followed by two elutions of 15 μL of buffer containing 500 mM EDTA and 500 mM NaCl. Elutions were analyzed by quantitative HPLC.

TABLE 5

|  | Elution 1 (%) | Elution 2 (%) |
|---|---|---|
| Rubredoxin-Spin | 13 | 64 |
| Rubredoxin- Standless Electronic Pipette | 67 | 23 |
| Ubiquitin-Spin | 9 | 52 |
| Ubiquitin- Standless Electronic Pipette. | 75 | 21 |

In summary, although all three modes gave good recovery of a variety of proteins purified with Protein G, Protein A and Ni-IMAC affinity resins, in every case the pipette tip columns when used in the back and forth flow mode delivered superior results to the spin column mode. When used in the 96-well plate an important advantage to using pipette tip columns is the ability to contain and track samples and buffers systematically. The protocol is efficient and significantly less prone to errors. Finally, protocols using plates and pipette tip columns with manual or standless electronic pipettes enabled true parallel processing of multiple test samples alongside one or more controls. Such protocols minimize or even eliminate errors through simplified workflow and structured analysis of experimental results.

Example 3

Process for Capture, Purification and Enrichment of Proteins Using Pipette Tip Columns The volumes stated in this process are for guideline purposes only and can change depending on the volume of the sample, the size of the column, the extent and type of washing and the type and amount of elution volume. The descriptions apply the control needed for pipette tip columns by an electron pipette with the appropriate firmware, software and programming. The programming adjustments will apply to many different types of columns including packed bed, encapsulated bed and monolith columns and including gel resins, polymer resins and silica or other inorganic based resins. But in general the processing steps are optional conditioning, capture, washing, optional additional washing steps and enrichment or elution. All of these steps are normally programmed using a computer. In order to program these into an electronic free standing pipette, the pipette must be modified to contain the appropriate microprocessing ability, firmware programming and storage, software programming and storage and interface. These microprocessing power needed goes far beyond what is required for pipetting and mixing operations and must be designed into the pipette.

Condition Tip

This step is to ensure that the tip is in a uniform ready condition. This may involve treating with a solvent and/or removing excess liquid from the bed. This may be done at the factory or directly prior to using the column. If agarose or similar materials are used, the bed must be kept fully hydrated before use. Air may be introduced into the bed at this stage (or any stage). But because of the need to control the movement of the liquid through the bed, it is generally not preferred except at this stage.

Step 1. A particular volume of air is drawn into the syringe. The volume amount depends on the type of tip used (e.g., 1000+ tip or 200+ tip).

Step 2. The tip itself is attached to the system (e.g., handheld, ME 100)

Step 3. The same volume of air as in Step 1 is expelled.

Step 4. A particular volume of air is drawn into the syringe again. This extra volume is used in various later steps throughout the method to allow extra expulsion of liquid. Optionally the tip may be removed and reattached to equalize pressure within the column.

Capture (Sample Loading)

This step can be performed with bi directional flow and as many cycles as needed may be used to ensure maximum or desired uptake. High linear velocities are used to reduce time needed for loading. Because of this, it is likely that most of the loading interactions are at the surface of the packing material. The linear velocity may have to be lowered for slow extraction reactions. After the loading, the excess liquid is expelled.

Step 5. The handheld is lowered into vials filled with sample (e.g., 200 uL of sample for 200+ pipette tip column).

Step 6. A particular volume of sample is drawn into the syringe.

Step 7. The same volume is expelled (one cycle completed).

Step 8. The same volume is drawn again into the syringe.

Step 9. A volume slightly greater than Step 8 is expelled (two cycles completed).

Purification (Washing)

The wash cycle is used to remove excess matrix material or to remove lightly adsorbed or non specific adsorbed materials so that they do not come off in the elution cycle and contaminate the analyte material. The wash cycle can involve solvents or solvent having a specific pH or containing components that that help remove materials which interact lightly with the extraction phase. In some cases, several wash solvents might be used in succession to remove specific material. These cycles may be repeated as many times as necessary. In other cases, where light contamination can be tolerated, a wash cycle may not be used. If a wash step is used, one or more solvents may be used. This example shows two solvents.

PBS Wash

Step 10. The handheld is raised, and vials are replaced with fresh vials of PBS wash solution.

Step 11. The handheld is lowered to begin the wash mode.

Step 12. A particular volume of PBS wash solution is drawn into the syringe.

Step 13. The same volume of solution is expelled (one cycle completed).

Step 14. The same volume of solution is drawn into the syringe again.

Step 15. A volume slightly greater than Step 14 is expelled (two cycles completed).

Water Wash

Step 16. The handheld pipette is raised, and vials are replaced with fresh vials of water. The handheld is lowered to finish the wash mode.

Step 17. A particular volume of water is drawn into the syringe.

Step 18. A volume slightly less than Step 17 is expelled (one cycle completed).

Step 19. The same volume of water as Step 17 is drawn into the syringe.

Step 20. A volume slightly greater than Step 19 is expelled (two cycles completed). The tip may be removed and reattached to equalize pressure within the column.

Enrichment (Elution)

Elution or desorption of the analyte is performed with as small volume as possible to maintain the concentration of the analyte in the final solution. This cycle may be repeated as many times as necessary. Step elutions may be performed to remove materials of interest in a sequential manner.

Step 21. The handheld is raised, and vials are replaced with fresh vials filled with Elution Solution.

Step 22. The handheld is lowered to begin Elution Mode.

Step 23. A particular volume of elution solution is drawn into the syringe.

Step 24. The same volume of solution is expelled (one cycle completed).

Step 25. The same volume of solution is drawn again.

Step 26. The same volume of solution is expelled (two cycles completed).

Step 27. The same volume of solution is drawn again.

Step 28. The same volume of solution is expelled (three cycles completed).

Step 29. The same volume of solution is drawn again.

Step 30. A volume slightly greater than Step 29 is expelled (four cycles completed).

Step 31. Sample vials now contain purified and enriched protein.

Example 4

Use of the Standless Pipette with Different Column Chemistries

This example is intended to illustrate how the firmware of an electronic pipette would be programmed to operate without computer control. The instructions could be used with Rainin handheld electronic pipettes such as a) EDP-3, SE-200, E8-200 and E-12-200 or b) EDP-3, SE-1000, E8-1000 and E-12-1000 for operation of pipette tip columns if this capability could be designed into these electronic pipettes. Appropriate terms and nomenclature would be different for different electronic pipette or electronic pipettes specifically designed for the use of pipette tip columns. The terms used in this example are chosen from those available with the display of these particular electronic pipette models.

Start operation. Set up deep-well plate with appropriate number and volumes of condition, sample, wash and elution volumes and aliquots. Program the pipette.

1. Hold down MODE until display flashes, Scroll with MODE until "PHY OFF" is displayed. Use ARROWS to select "ON." Press RESET to activate PhyNexus operation mode.

2. To run the saved program, go to step 12, or begin reprogramming at Step 3.

3. Press RESET to display "FLO." Use ARROWS to set Flow Rate of 1=Low, 2=Medium or 3=High. Medium speed is recommended.

4a. Press RESET to display "CAP." Use ARROWS to set the Capture Volume between 40-200 uL.

4b. Press RESET to display "CAP." Use ARROWS to set the Capture Volume between 230-1000 uL 5. Press RESET to display CAP nbr1. Use ARROWS to set the number for capture fractions 1-2, equivalent to the number of wells containing sample aliquots.

6. Press RESET to display CAP CYC1." Use ARROWS to set the number of Capture Cycles per well to 1-8. Each sample well will be processed by this number of cycles. 4 capture cycles are recommended.

7a. Press RESET to display "Pur." Use ARROWS to set Wash Volume to 40-200 uL.

7b. Press RESET to display "Pur." Use ARROWS to set Wash Volume to 230-1000 uL.

8. Press RESET to display "Pur nbr1." Use ARROWS to set Number of Washes to 1 or 2, equivalent to the number of separate wash wells. Each wash well will be processes by 2 wash cycles.

9a. Press RESET to display "ELU." Use ARROWS to set Elution Volume to 10-200 uL.

9b. Press RESET to display "ELU." Use ARROWS to set Elution Volume to 230-1000 uL.

10. Press RESET to advance to "ELU nbr1." Use ARROWS to set the Number of Elution Fractions to 1 or 2 for each separate well. Each elution fraction will be processed by 4 elution cycles.

11. Press RESET to display "YES SAVE." Use ARROWS to select Save Program YES or NO. If YES, rewrite current program. If NO, run program, but do not save over saved program. (Note if enough memory is available, then pipette can save more than 1 program).

12. Press TRIGGER to display "PHY" which signifies ready to run. Pipette will beep.

13. Attach Pipette tip column(s) and submerge standless pipette with columns into the sample wells in the deep-well plate. Press TRIGGER. Pipette will display "CAP nbr1" and beep after processing the specified number of capture cycles. Pipette will display "CAP nbr2" if user specified more than 1 capture fraction. Move pipette tip columns to next capture well and press TRIGGER. Repeat until Pipette beeps and displays "Pur nbr1."

14. Move standless pipette with columns into the wash wells in the deep-well plate. Press TRIGGER to run wash. Pipette will display "Pur nbr1" and beep after 2 flow cycles. If programmed to run additional washes, the pipette will display "pur nbr2." Move the columns to the next wash well and press TRIGGER as guided. Pipette will beep when wash if finished.

15. When pipette displays "ELU nbr1" move the standless pipette with columns to the first elution well. Press TRIGGER to run elution. The pipette will beep after 2 elution cycles are finished. Pipette will display "ELU nbr2" if programmed for an additional elution aliquot was programmed. Move pipette with columns to the next elution well and press TRIGGER.

16a. Pipette will beep to signal the end of the final elution and will display "done". Remove pipette with columns and dispose of columns. Press TRIGGER to begin the next set of purifications. Add new columns and go to step 13 to start the operation.

16b. Pipette will beep to signal the end of the final elution and will display "done". Remove pipette with columns and dispose of columns. Press RESET to reprogram and begin a new purification method. Go to step 3 to start operation.

Example 5

Plasmid DNA Prep Procedure Using Pipette Tip Columns with a Standless Pipette and Deep-Well Plate was Used to Purify Plasmids from Cell Culture Pipette tip columns of silica can purify up to 10 μg of plasmid DNA. The purified plasmid is compatible with any downstream application including DNA sequencing, PCR amplification, transformation and restriction enzyme digestion.
Set Up Deep-Well Plates as Follows:
Plate 1
Row 1: Deep-well block row of preparation from step 4 of procedure below.
Row 2: Deep-well block row containing 300 uL of Resuspension buffer
Row 3: Deep-well block row containing 300 uL of Lysis buffer
Row 4: Deep-well block row containing 400 uL of Neutralizing buffer
Plate 2
Row 1: Deep-well block row containing 200 uL of Equilibration buffer
Row 2: Deep-well block row containing 200 uL of Wash 1 buffer
Row 3: Deep-well block row containing 200 uL of Wash 2 buffer
Row 4: Deep-well block row containing 200 uL of Elution buffer
Procedure:
Grow Cells:
1. Grow a single plasmid containing *E. coli* bacterial colony in 800 uL of 2×YT bacterial growth medium in 96-well 2 mL deep-well culture block.
2. Cover the plate with a gas permeable seal and shake at 300 rpm at 37° C. for 17.5 hours.
3. Pellet bacterial cultures by centrifuging culture plate at 2500×g for 10 minutes.
4. After centrifugation, remove the seal and invert the block to decant the media away from the cell pellets. Blot the inverted block on a paper towel to remove excess media.
Lyse the Cells Harboring the Plasmid.
Add 250 uL of Re-suspension buffer to pellet bacterial culture using standard pipette and tips in normal manner.
1. Re-suspend the pellet completely by standard pipette mixing. Use slow and fast flow rates to re-suspend.
2. Add 250 uL of Lysis buffer to re-suspended culture using gentle pipette mixing for 3 minutes.
3. Add 350 uL of Neutralization buffer to lysed culture using gentle pipette mixing for 3 minutes.
4. Spin down plate to remove particulate and clarify lysate.
Standless Pipette and Pipette Tip Column Method:
1. Transfer 600 uL clarified lysate to deep-well block making certain not to disturb particulate.
2. Program the modified pipette and attach a pipette tip column containing silica resin.
3. Equilibrate the pipette tip columns by cycling through the equilibration buffer. Use 2 cycles at 0.5 mL/min flow rate.
4. Capture the plasmid DNA. Use 8 cycles at 0.25 mL/min flow rate.
5. Wash (Wash 1 buffer) the captured plasmid DNA. Use 2 cycles at 0.5 mL/min flow rate.
6. Wash (Wash 2 buffer) the captured plasmid DNA. Use 2 cycles at 0.5 mL/min flow rate.
7. Elute the captured plasmid DNA. Use 8 cycles at 0.25 mL/min flow rate.

Example 6

A Pipette Tip Made from a Syringe

In this example, a pipette tip column was made from the barrel of a 1 mL disposable syringe. First, the lower end of the column was shaved diagonally on the outer side to produce a chamfered or beveled edge. Next, a top frit was inserted into the column through the lower end of the column as follows. A sheet of frit material comprised of 90 micron porous polypropylene, 1/16-inch thick was pushed against the end of the tube, cutting the frit into a circle having the diameter of the inside of the column and pushing the frit into the column body. The frit remained in the column tube by friction fit.

To put the solid phase into the column, Captor Q agarose/Sepharose ion exchange resin, 50% slurry in water, was placed in a beaker. The top of the column was fitted with a Cole Parmer female luer thread style to 200 series barb 1/8 inch 3.2 mm. The top frit was pushed then into the column body until a chamber of approximately 200 μL was formed. A 1 mL Hamilton gas tight glass syringe was placed on the top of the column and the lower end of the column was placed in the resin slurry. 200 μL of resin was pulled into the column bed chamber.

To make the bottom frit, the end of the column was placed against the sheet of porous polymer polypropylene sheet. Applying pressure a frit was cut and forced into the column body with the bottom surface of the frit flush with the end of the column. Then, the luer fitting was removed from the end of the column. A metal tube with approximately 1/16 inch diameter, which was approximately one half of the column diameter, was used to push the top frit down until the chamber was approximately 100 μL and filled, but loosely packed, with the resin.

Example 7

Manual Processing of Blood

The pipette tip column fabricated in Example 6 was used to process a blood sample. The luer fitting with barbed fitting was reinserted into the column and the Hamilton syringe attached to the column. The end of the column was place into approximately 0.75 mL of Bovine whole blood stabilized with EDTA from BioreclamationIVT Catalog number BOVWBEDTA. The blood sample was processed through the column with back and forth flow with manual manipulation of the syringe. Blood entered and exited the column through the lower end of the column. Then the column was placed in several aliquots of DI water and processed with back and forth flow through the column. There was a complete washing of column and frit with no visible retention of blood on column wall, column bed, or frit.

Example 8

Automated Processing of Blood

The pipette tip column fabricated in Example 6 is operated using a computer-controlled syringe with fully contained firmware and software.

While the invention has been described in connection with specific embodiments thereof, it will be understood that it is capable of further modifications and this application is intended to cover any variations, uses, or adaptations of the invention that follow, in general, the principles of the invention, including such departures from the present disclosure as come within known or customary practice within the art to which the invention pertains and as may be applied to the essential features hereinbefore set forth. Moreover, the fact that certain aspects of the invention are pointed out as preferred embodiments is not intended to in any way limit the invention to such preferred embodiments.

We claim:

1. An apparatus for operating pipette tip columns, comprised of:
   a) a deep well microplate having a plurality of wells;
   b) a plurality of pipette tip columns, wherein each column has an open upper end, an open lower end, and a solid phase therebetween, wherein the solid phase is comprised of a functional group having affinity for cells, wherein each pipette tip column is positioned within a well of the deep well microplate in such a way that the pipette tip column is approximately centered within the well and the open lower end of the pipette tip column does not form a seal with the bottom of the deep well microplate well that prevents liquid flow into or out of the open lower end of the pipette tip column;
   c) an electronic multichannel pipette, wherein the electronic multichannel pipette is comprised of firmware and software, wherein the electronic multichannel pipette is capable of pipette tip column operation, wherein the open upper ends of the pipette tip columns are independently engaged with the electronic multichannel pipette in such a way that a stand is not required to support the electronic multichannel pipette and a hand is not required to support the electronic multichannel pipette, wherein the electronic multichannel pipette will not tip over and wherein the electronic multichannel pipette is situated at an angle that is 35 degrees or less from vertical; and
   d) a base, wherein the deep well microplate is secured to the base, and wherein the base has sufficient area to keep the deep well microplate from falling over when the pipette tip columns are positioned within the wells of the deep well microplate and the pipette tip columns are engaged with the electronic multichannel pipette.

2. The apparatus of claim 1, wherein the functional group is an antibody or aptamer.

3. The apparatus of claim 1, wherein the deep well microplate is a 96-well plate.

4. The apparatus of claim 1, wherein the deep well microplate contains a solution selected from the group consisting of a sample solution, a wash solution and a desorption solution.

5. A method for purifying an analyte from a sample solution using the apparatus of claim 1, comprising:
   a) placing the sample solution into some wells of the deep well microplate, wherein the sample solution is comprised of cells;
   b) optionally, placing a wash solution into some wells of the deep well microplate;
   c) placing a desorption solution into some wells of the deep well microplate;
   d) placing the open lower ends of the pipette tip columns into the sample solution and aspirating and expelling the sample solution;
   e) optionally, placing the open lower ends of the pipette tip columns into the wash solution and aspirating and expelling the wash solution; and
   f) placing the open lower ends of the pipette tip columns into the desorption solution and aspirating and expelling the desorption solution.

6. The method of claim 5, wherein the sample is whole blood.

7. The method of claim 5, wherein the cells are selected from the group consisting of B cells, T cells and stem cells.

8. The method of claim 5, wherein the cells are engineered.

9. The method of claim 5, wherein the cells are viable.

10. The method of claim 5, wherein the sample solution, the wash solution or the desorption solution are aspirated and expelled from the pipette tip columns repeatedly.

11. An apparatus for operating pipette tip columns, comprised of:
   a) a microplate having a plurality of wells;
   b) at least one plate modifier, wherein the plate modifier has an upper end and a lower end and a channel therethrough, wherein the upper end of the plate modifier rests on top of the microplate, wherein the lower end the plate modifier is fitted within the well of the microplate;
   c) at least one pipette tip column having an open upper end, an open lower end, and a solid phase therebetween, wherein the solid phase is comprised of a functional group having affinity for cells, wherein the pipette tip column is engaged within the channel of the plate modifier in such a way that the open lower end of the pipette tip column does not form a seal with the bottom of the microplate well that prevents liquid flow into or out of the open lower end of the pipette tip column; and
   d) an electronic pipette, wherein the electronic pipette is comprised of firmware and software, wherein the electronic pipette is capable of pipette tip column operation, wherein the open upper end of the pipette tip column is engaged with the electronic pipette in such a way that a stand is not required to support the electronic pipette and a hand is not required to support the electronic pipette.

12. The apparatus of claim 11, wherein the microplate is a 96-well deep-well plate.

13. The apparatus of claim 11 wherein the microplate contains a solution selected from the group consisting of a sample solution, a wash solution and a desorption solution.

14. The apparatus of claim 11, wherein the functional group is an antibody or aptamer.

15. A method for purifying an analyte from a sample solution using the apparatus of claim 11, comprising:
   a) placing the sample solution into some wells of the deep well microplate, wherein the sample solution is comprised of cells;
   b) optionally, placing a wash solution into some wells of the deep well microplate;
   c) placing a desorption solution into some wells of the deep well microplate;
   d) placing the open lower end of the pipette tip column into the sample solution and aspirating and expelling the sample solution;
   e) optionally, placing the open lower end of the pipette tip column into the wash solution and aspirating and expelling the wash solution; and f) placing the open lower end of the pipette tip column into the desorption solution and aspirating and expelling the desorption solution.

16. The method of claim 15 wherein the sample solution, the wash solution or the desorption solution are aspirated and expelled from the pipette tip column repeatedly.

17. The method of claim 15, wherein the sample is whole blood.

18. The method of claim 15, wherein the cells are selected from the group consisting of B cells, T cells and stem cells.

19. The method of claim 15, wherein the cells are engineered.

20. The method of claim 15, wherein the cells are viable.

21. The method of claim 5, wherein the method is performed under sterile conditions.

22. The method of claim 15, wherein the method is performed under sterile conditions.

* * * * *